United States Patent [19]

Forestier et al.

[11] Patent Number: 5,538,716
[45] Date of Patent: Jul. 23, 1996

[54] PHOTOSTABLE COSMETIC SCREENING COMPOSITION CONTAINING A UV-A SCREENING AGENT AND A (4-METHOXYBENZYLIDENE)CYANOACETATE

[75] Inventors: Serge Forestier, Claye-Souilly; Andre Deflandre, Orry-La-Ville, both of France

[73] Assignee: L'Oreal, Paris, France

[21] Appl. No.: 39,047

[22] PCT Filed: Aug. 5, 1992

[86] PCT No.: PCT/FR92/00774

§ 371 Date: Apr. 7, 1993

§ 102(e) Date: Apr. 7, 1993

[87] PCT Pub. No.: WO93/02659

PCT Pub. Date: Feb. 18, 1993

[30] Foreign Application Priority Data

Aug. 7, 1991 [FR] France ................. 91 10061

[51] Int. Cl.$^6$ ............... A61K 7/42; C07C 255/02
[52] U.S. Cl. ............................ 424/59; 558/401
[58] Field of Search ................. 558/401; 424/59

[56] References Cited

U.S. PATENT DOCUMENTS

| | | | |
|---|---|---|---|
| 3,180,885 | 4/1965 | Nenteoig et al. | 558/401 |
| 3,256,312 | 6/1966 | Strobel et al. | 558/401 |
| 3,278,448 | 10/1966 | Lauerer et al. | 558/401 |
| 3,280,069 | 8/1966 | Knapp et al. | 558/401 |
| 3,462,475 | 8/1969 | Strobel et al. | 558/401 |
| 3,546,270 | 12/1970 | Kirchmayr et al. | 558/401 |
| 4,894,222 | 1/1990 | Matraners | 424/59 |
| 4,940,574 | 7/1990 | Kaplan | 424/59 |

FOREIGN PATENT DOCUMENTS

| | | |
|---|---|---|
| 0005182 | 11/1979 | European Pat. Off. . |
| 2440933 | 6/1980 | France . |
| 2198944 | 6/1988 | United Kingdom . |
| WO91/11989 | 8/1991 | WIPO . |

Primary Examiner—Shelley A. Dodson
Attorney, Agent, or Firm—Jacobson, Price, Holman & Stern

[57] ABSTRACT

A photostable cosmetic composition for protecting the human epidermis against UV radiation comprises, in a cosmetically acceptable carrier, from 0.5 to 5% by weight of 4-(1,1-dimethylethyl)-4'-methoxydibenzoylmethane and at least 0.5% by weight of a compound of formula (I):

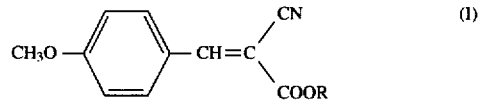

where R stands for an alkyl radical, the molar ratio of the compound of formula (I) to 4-(1,1-dimethylethyl)-4'-methoxydibenzoylmethane being 0.8 or over.

14 Claims, No Drawings

PHOTOSTABLE COSMETIC SCREENING COMPOSITION CONTAINING A UV-A SCREENING AGENT AND A (4-METHOXYBENZYLIDENE)CYANOACETATE

The present invention relates to a photostable cosmetic composition intended for protecting the skin against UV radiation, containing a UV-A screening agent and a (4-methoxybenzylidene)cyanoacetate, to its use for protection of the skin against UV rays and to a process for stabilizing the UV-A screening agent with a (4-methoxybenzylidene)cyanoacetate.

UV-A rays of wavelengths between 320 and 400 nm, causing tanning of the skin, are known to be capable of inducing unwelcome changes in the latter, in particular in the case of sensitive skin or skin continually exposed to solar radiation. UV-A rays cause, in particular, a loss of elasticity of the skin and the appearance of wrinkles leading to a premature ageing. They promote a triggering of the erythematous reaction or enhance this reaction in certain subjects, and can even be the source of phototoxic or photoallergic reactions. It is hence desirable to screen out the UV-A radiation.

French Patent No. 2,440,933 describes 4-(1,1-dimethylethyl)-4'-methoxydibenzoylmethane as a UV-A screening agent. The proposal is made to combine this particular UV-A screening agent, sold by the company GIVAUDAN under the name "PARSOL 1789", with various UV-B screening agents with the object of absorbing all the UV radiation of wavelengths between 280 and 380 nm.

Unfortunately, when this UV-A screening agent is used alone or in combination with UV-B screening agents, it does not possess satisfactory photochemical stability for assuring constant protection of the skin during prolonged exposure to the sun, thereby necessitating repeated applications at regular and frequent intervals if it is desired to obtain effective protection of the skin against all UV rays.

The Applicant discovered that, by combining 4-(1,1-dimethylethyl)-4'-methoxydibenzoylmethane with a UV-A screening agent of the (4-methoxybenzylidene)cyanoacetate type of formula:

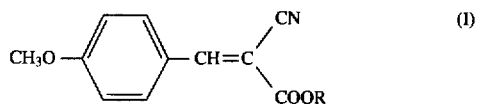

in proportions and in a mole ratio that are well defined, photochemical stability of 4-(1,1-dimethylethyl)-4'-methoxydibenzoylmethane was surprisingly obtained. A stabilized combination protecting the human epidermis against UV rays of wavelengths between 320 and 380 nm is thereby obtained. This combination is especially advantageous in skin care products for daily use with the object of retarding skin ageing.

Photostable antisun compositions that screen out all UV rays of wavelengths between 280 and 380 nm can be obtained by adding UV-B screening agents to the abovementioned combination of UV-A screening agents.

In the general formula (I), the substituent R represents a linear or branched alkyl radical containing 6 to 12 carbon atoms.

n-Hexyl, n-octyl, n-decyl, n-dodecyl, isooctyl, isononyl and isodecyl radicals may be mentioned, for example.

Among the compounds of formula (I), the following are more especially preferred:

- n-hexyl (4-methoxybenzylidene)cyanoacetate,
- isononyl (4-methoxybenzylidene)cyanoacetate.

The compounds of formula (I) together with a process for preparing them are described in Application EP 0,005,182.

As a result of their lipophilic nature, the screening agents used distribute uniformly in the traditional cosmetic carriers containing at least one fatty phase or which take the form of aqueous dispersions of lipid vesicles, and can thus be applied to the skin to form an effective protective film.

The subject of the present invention is a photostable cosmetic composition that protects the skin against UV radiation of wavelengths between 320 and 380 nm, comprising, in a cosmetically acceptable carrier, from 0.5 to 5% by weight of 4-(1,1-dimethylethyl)-4'-methoxydibenzoylmethane and at least 0.5% by weight of compound of formula (I), the mole ratio of the compound of formula (I) to 4-(1,1-dimethylethyl)-4'-methoxydibenzoylmethane being greater than or equal to 0.8, and preferably greater than or equal to 1.2.

The upper limit of this mole ratio is determined by the solubility of these screening agents in the fatty phase used in the composition, or in the lipid phase present in the vesicular dispersion.

The subject of the present invention is also a process for protecting the human epidermis against the effects of UV rays of wavelengths between 320 and 380 nm, consisting in applying an effective amount of the cosmetic composition as defined above to the skin.

Another subject of the present invention consists of a process for stabilizing 4-(1,1-dimethylethyl)-4'-methoxydibenzoylmethane against UV radiation using a compound of formula (I), in which process at least 0.5% by weight of compound of formula (I) is used to stabilize from 0.5 to 5% by weight of 4-(1,1-dimethylethyl)-4'-methoxydibenzoylmethane, the mole ratio of the compound of the formula (I) to 4-(1,1-dimethylethyl)-4'-methoxydibenzoylmethane being equal to or greater than 0.8.

The cosmetic compositions according to the invention can take the form of oily or oleoalcoholic lotions, or the form of fatty or oleoalcoholic gels, of solid sticks, of emulsions such as a cream or a milk or of vesicular dispersions of ionic or nonionic amphiphilic lipids; they can be packaged as an aerosol.

As a solubilizing solvent, an oil or a wax, a monohydric alcohol or a lower polyol or a mixture thereof may be used. Especially preferred monohydric alcohols or polyols are ethanol, isopropanol, propylene glycol and glycerol.

The cosmetic composition according to the invention, intended for protecting the human epidermis against ultraviolet rays, can contain cosmetic adjuvants that are common in this type of composition, such as thickeners, emollients, humectants, surfactants, preservatives, antifoams, oils, waxes, lanolin, perfumes, propellants, dyes and/or pigments whose function is to color the composition itself or the skin, or any other ingredient customarily used in cosmetics.

One embodiment of the invention is an emulsion in the form of a cream or milk comprising, in addition to the compound of the formula (I) combined with 4-(1,1-dimethylethyl)- 4'-methoxydibenzoylmethane, fatty alcohols, fatty acid esters, and in particular fatty acid triglycerides, fatty acids, lanolin, oils, natural or synthetic waxes and emulsifiers, in the presence of water.

Another embodiment consists of oily lotions based on fatty acid esters, on natural or synthetic oils and/or waxes, or oleoalcoholic lotions based on oils, on waxes or on fatty acid esters such as the triglycerides of fatty acids and of lower alcohols such as ethanol or of glycols such as propylene glycol and/or of polyols such as glycerol.

The oleoalcoholic gels comprise an oil or a wax, an alcohol or a lower polyol, such as ethanol, propylene glycol or glycerol, and a thickener such as silica.

The solid sticks consist of fats such as natural or synthetic waxes and oils, fatty alcohols, fatty acid esters and lanolin.

The vesicular dispersions of ionic or nonionic amphiphilic lipids are prepared according to known processes, such as, for example, by causing the lipids to swell in an aqueous solution to form spherules dispersed in the aqueous medium, as described in the paper by BANGHAN, STANDISH and WATKINS, J. Mol. Biol., 13, 238 (1965) or in the Applicant's Patents FR 2,315,991 and 2,416,008. A description of the various methods of preparation will be found in "Les liposomes en biologie cellulaire et pharmacologie" [Liposomes in cell biology and pharmacology], Edition INSERM/ John Libbery Eurotext, 1987, pages 6 to 18.

When the compositions take the form of an emulsion or vesicular dispersion, the aqueous phase can contain, in addition, water-soluble UV screening agents such as benzene-1,4-[di(3-methylidene-10-camphorsulfonic acid)] [sic], 2-phenylbenzimidazole-5-sulfonic acid or 2-hydroxy-4-methoxybenzophenone-5-sulfonic acid, these acids being salified or otherwise.

In the case of a composition packaged as an aerosol, traditional propellants such as alkanes, fluoroalkanes and chlorofluoroalkanes are used.

The compositions according to the invention can also contain metal oxide nanopigments dispersed in the fatty phase and/or in the aqueous phase.

Another subject of the present invention consists of a photostable cosmetic antisun composition that screens out UV rays of wavelengths between 280 and 380 nm, characterized in that it contains UV-B screening agents in addition to the combination of UV-A screening agents as is defined above.

The present invention also relates to a process for protecting the human epidermis against the effects of UV rays of wavelengths between 280 and 380 nm, consisting in applying an effective amount of a composition containing UVB [sic] screening agents and the combination of 4-(1,1-dimethylethyl)-4'-methoxydibenzoylmethane and compounds of formula (I).

As a UV-B screening agent, there may be mentioned, for example, benzylidenecamphor and its derivatives such as p-methylbenzylidenecamphor; β,β-diphenylacrylates; alkyl α-cyano-β,β-diphenylacrylates such as 2-ethylhexyl α-cyano-β,β-diphenylacrylate; dialkyl benzalmalonates; salicylic acid esters; p-aminobenzoic acid esters and their derivatives; and benzophenone derivatives such as 2-hydroxy-4-methoxybenzophenone and 2,2'-dihydroxy-4'-methoxybenzophenone.

These UV-B screening agents are present in concentrations not exceeding 10% by weight of the total weight of the composition, and preferably between 0.5 and 8% by weight.

The antisun compositions of the invention can take the same forms as the compositions for daily use for protection of the human epidermis.

The examples which follow serve to illustrate the invention without, however, any limitation being implied.

EXAMPLE 1 TO 4

| CONSTITUENTS (in g) | Ex. 1 | Ex. 2 | Ex. 3 | Ex. 4 |
|---|---|---|---|---|
| 4-(1,1-dimethylethyl)-4'-methoxydibenzoylmethane | 1.5 | 1.5 | 1.5 | 1.75 |
| n-hexyl (4-methoxybenzylidene)cyanoacetate | 4.5 | — | 2.0 | 8.0 |
| isononyl (4-methoxybenzylidene)cyanoacetate | — | 4.5 | — | — |

EXAMPLE 1 TO 4 -continued

| CONSTITUENTS (in g) | Ex. 1 | Ex. 2 | Ex. 3 | Ex. 4 |
|---|---|---|---|---|
| Mixture of cetyl/stearyl alcohol and oxyethylenated cetyl/stearyl alcohol containing 33 mol of EO (1) | 7.0 | 7.0 | 7.0 | 7.0 |
| Mixture of stearates of mono-, di- and triglycerol [sic] | 2.0 | 2.0 | 2.0 | 2.0 |
| $C_8$–$C_{12}$ fatty acid triglycerides | 30.0 | 30.0 | 30.0 | 30.0 |
| Polydimethylsiloxane | 1.5 | 1.5 | 1.5 | 1.5 |
| Cetyl alcohol | 1.5 | 1.5 | 1.5 | 1.5 |
| Distilled water QS | 100 | 100 | 100 | 100 |

The emulsions of Examples 1 to 4 are prepared according to traditional techniques, by dissolving the screening agents in the fatty phase containing the emulsifiers, heating this fatty phase to about 80°–85° C. and adding, with vigorous stirring, water previously heated to about 80° C. These emulsions constitute day creams for protecting the human epidermis.

EXAMPLE 5

| | |
|---|---|
| Polyglycerolate (3 mol) cetyl alcohol | 3.8 g |
| Cholesterol | 3.8 g |
| Monosodium salt of the glutamate of formula: | 0.4 g |

$$HOOC-CH_2-CH_2CH-COONa$$
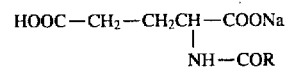
$$NH-COR$$

| | |
|---|---|
| in which R is a mixture of $C_{14}$–$C_{22}$ hydrogenated alkyl and/or alkenyl radicals which is derived from tallow fatty acids, sold by company AJINOMOTO under the trade name "ACYLGLUTAMATE HS 11" | |
| Glycerol | 2.0 g |
| Benzene-1,4-di(3-methylidene-10-camphor-sulfonic acid) [sic] in aqueous solution containing 35% AS | 1.0 g AS |
| Triethanolamine | 0.6 g |
| Benzoate of $C_{12}$–$C_{15}$ alcohols, sold by the company WITCO under the name "FINSOLV TN" | 8.0 g |
| Cyclotetradimethylsiloxane | 5.0 g |
| 4-(1,1-Dimethylethyl)-4'-methoxydibenzoylmethane | 2.0 g |
| n-Hexyl (4-methoxybenzylidene)cyanoacetate | 4.0 g |
| Hydroxyethylcellulose modified with a cetyl chain, sold by the company AQUALON under the name "NATROSOL PLUS GRADE 330 CS" | 0.5 g |
| Preservatives, sequestering agent qs | |
| Water qs | 100 g |

EXAMPLE 6

| | |
|---|---|
| Mixture (80:20) of cetyl/stearyl alcohol and oxyethylenated cetyl/stearyl alcohol containing 33 mol of ethylene oxide, sold by the company HENKEL under the name "SINNOWAX AO" | 7.0 g |
| Glyceryl mono- and distearate (40:50) | 2.0 g |
| Cetyl alcohol | 1.5 g |
| DOW CORNING silicone oil DC 200–350 cst | 1.5 g |
| Liquid paraffin | 15.0 g |
| 4-(1,1-dimethylethyl)-4'-methoxydibenzoylmethane | 1.0 g |
| n-Hexyl (4-methoxybenzylidene)cyanoacetate | 3.0 g |

-continued

EXAMPLE 6

| | |
|---|---|
| Alumina- and aluminum stearate-coated titanium oxide sold by the company TAYCA under the name "MICRO TITANIUM DIOXIDE MT 100T" | 2.0 g |
| Glycerol | 20.0 g |
| Preservatives, sequestering agent, perfume qs | |
| Water qs | 100 g |

We claim:

1. Photostable cosmetic screening composition for protection of the human epidermis against ultraviolet rays of wavelengths between 320 and 380 nm, which comprises, in a cosmetically acceptable carrier, from 0.5 to 5% by weight of 4-(1,1-dimethylethyl)- 4'-methoxydibenzoylmethane and at least 0.5% by weight of a (4-methoxybenzylidene)cyanoacetate of formula:

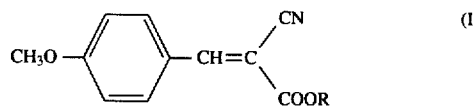

where R denotes a linear or branched alkyl radical having 6 to 12 carbon atoms; the mole ratio of the compound of formula (I) to 4-(1,1-dimethylethyl)-4'-methoxydibenzoylmethane being greater than or equal to 0.8.

2. Composition according to claim 1, wherein the compound of formula (I) is selected from the group consisting of n-hexyl (4-methoxybenzylidene)cyanoacetate and isononyl (4-methoxybenzylidene)cyanoacetate.

3. Composition according to claim 1, which is conditioned under a form selected from the group consisting of an oily or oleoalcoholic lotion, a fatty or oleoalcoholic gel, a solid stick, an emulsion, a vesicular dispersion of ionic or nonionic amphiphilic lipids, and an aerosol.

4. Composition according to claim 1, which contains, in addition, a cosmetic adjuvant selected from the group consisting of thickeners, emollients, humectants, surfactants, preservatives, antifoams, perfumes, oils, waves, lower polyols and monohydric alcohols, propellants, dyes and pigments.

5. Composition according to claim 1, which is an emulsion in the form of a cream or milk comprising a cosmetic carrier selected from the group consisting of fatty alcohols, fatty acid esters, fatty acids, lanolin, natural or synthetic oils and waxes and emulsifiers, in the presence of water.

6. Composition according to claim 1, which is an oily lotion comprising a cosmetic carrier selected from the group consisting of fatty acid esters, natural or synthetic oils and waxes.

7. Composition according to claim 1, which is an oleoalcoholic lotion comprising a cosmetic carrier selected from the group consisting of oils, waxes and fatty acid esters.

8. Composition according to claim 1 in the form of an emulsion or vesicular dispersion of ionic or nonionic amphiphilic lipids, which contains, in addition, a water-soluble UV-screening agent selected from the group consisting of 1,4-[di(3-methylidene- 10-camphorsulfonic acid)], 2-phenylbenzimidazole-5-sulfonic acid and 2-hydroxy-4-methoxybenzophenone-5-sulfonic acid or their salts, the said water-soluble UV-screening agent being dispersed in the aqueous phase.

9. Composition according to claim 1 which contains, in addition, metal oxide nanopigments dispersed in the fatty phase and/or in the aqueous phase.

10. Cosmetic screening composition according to claim 1, which is an oleoalcoholic gel comprising a cosmetic carrier selected from the group consisting of a natural or synthetic oil, a lower polyol or alcohol and a thickener.

11. Process for protecting the human epidermis against the effects of UV rays of wavelengths between 320 and 380 nm, which consists in applying an effective amount of a cosmetic screening composition as defined in claim 1 to the skin.

12. Photostable cosmetic screening composition for protection of the human epidermis against UV rays of wavelengths between 280 and 380 nm, which comprises, in a cosmetically acceptable carrier, from 0.5 to 5% by weight of 4-(1,1-dimethylethyl)-4'-methoxy-dibenzoylmethane and at least 0.5% by weight of a (4-methoxybenzylidene)cyanoacetate of formula:

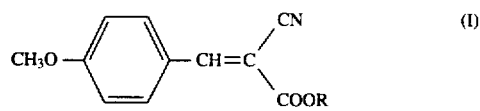

where R denotes a linear or branched alkyl radical having 6 to 12 carbon atoms; the mole ratio of the compound of formula (I) to 4-( 1,1-dimethylethyl)-4'-methoxydibenzoylmethane being greater than or equal to 0.8, and one or more UV-B screening agents selected from the group consisting of benzylidenecamphor and its derivatives; β,β-diphenylacrylates; dialkyl benzalmalonates; salicylic acid esters; p-aminobenzoic acid esters and their derivatives, benzophenone derivatives and alkyl α-cyano-β,β-diphenylacrylates.

13. Process for protecting the human epidermis against the effects of UV rays of wavelengths between 280 and 380 nm, which consists in applying an effective amount of a composition as defined in claim 12 to the skin.

14. In an improved photostable cosmetic screening composition for protection of the human epidermis against ultraviolet rays of wavelengths between 320 and 380 nm which comprises, in a cosmetically acceptable carrier, 4-(1, 1-dimethylethyl)- 4'-methoxydibenzoylmethane, wherein the improvement consists essentially of adding at least 0.5% by weight of a (4'-methoxy benzylidene)cyano acetate of formula (I)

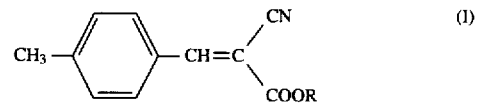

wherein R denotes a linear or branched alkyl radical having 6 to 12 carbon atoms, to said cosmetically acceptable carrier comprising 0.5 to 5% by weight of 4-(1,1-dimethylethyl)-4'-methoxydibenzoylmethane, the mole ratio of the compound of formula (I) to 4-(1,1-dimethylethyl) 4'-methoxy-dibenzoylmethane being greater than or equal to 0.8, whereby said dibenzoylmethane is stabilized against ultraviolet rays.

* * * * *